United States Patent
Park et al.

(10) Patent No.: US 9,121,042 B2
(45) Date of Patent: Sep. 1, 2015

(54) ENZYME USED IN BIOSYNTHESIS OF 1, 4-BDO AND SCREENING METHOD OF THE SAME

(71) Applicants: Samsung Electronics Co. Ltd., Suwon-si, Gyeonggi-do (KR); Ajou University Industry-Academic Cooperation Foundation, Suwon-si, Gyeonggi-do (KR)

(72) Inventors: Jin-hwan Park, Suwon-si (KR); Pyung-cheon Lee, Suwon-si (KR); Jae-chan Park, Yongin-si (KR); Young-min Lee, Suwon-si (KR); Woo-yong Lee, Hwaseong-si (KR)

(73) Assignees: SAMSUNG ELECTRONICS CO., LTD., Suwon-Si (KR); AJOU UNIVERSITY INDUSTRY-ACADEMIC COOPERATION FOUNDATION, Suwon-Si (KR)

( * ) Notice: Subject to any disclaimer, the term of this patent is extended or adjusted under 35 U.S.C. 154(b) by 96 days.

(21) Appl. No.: 13/954,696

(22) Filed: Jul. 30, 2013

(65) Prior Publication Data
US 2014/0045232 A1 Feb. 13, 2014

(30) Foreign Application Priority Data
Jul. 30, 2012 (KR) ........................ 10-2012-0083513

(51) Int. Cl.
| | | |
|---|---|---|
| C12P 7/24 | (2006.01) |
| C12N 9/42 | (2006.01) |
| C12N 1/20 | (2006.01) |
| C12N 15/00 | (2006.01) |
| C07H 21/04 | (2006.01) |
| C12P 7/18 | (2006.01) |
| C12N 9/04 | (2006.01) |
| C12N 9/02 | (2006.01) |

(52) U.S. Cl.
CPC ................. *C12P 7/18* (2013.01); *C12N 9/0006* (2013.01); *C12N 9/0008* (2013.01); *C12P 7/24* (2013.01)

(58) Field of Classification Search
CPC ............................................... C12Y 102/01057
USPC ............................. 435/147, 190, 252.3, 320.1
See application file for complete search history.

(56) References Cited

U.S. PATENT DOCUMENTS

| | | | |
|---|---|---|---|
| 7,858,350 | B2 | 12/2010 | Burk et al. |
| 7,947,483 | B2 | 5/2011 | Burgard et al. |
| 8,129,169 | B2 | 3/2012 | Van Dien et al. |

FOREIGN PATENT DOCUMENTS

| | | |
|---|---|---|
| KR | 1020070096348 A | 10/2007 |
| KR | 1020110135261 A | 12/2011 |

OTHER PUBLICATIONS

Yim et al., "Metabolic engineering of *Escherichia coli* for direct production of 1,4-butanediol," *Nature Chemical Biology*, 7: 445-452 (2011).

*Primary Examiner* — Tekchand Saidha
(74) *Attorney, Agent, or Firm* — Leydig, Voit & Mayer, Ltd.

(57) ABSTRACT

Recombinant butyraldehyde dehydrogenases (Blds) with improved production of 1,4-BDO, as well as recombinant microorganisms comprising polynucleotides encoding the recombinant Blds, and methods of producing 1,4-BDO by using the recombinant microorganisms.

21 Claims, 6 Drawing Sheets

FIG. 5

ENZYME USED IN BIOSYNTHESIS OF 1, 4-BDO AND SCREENING METHOD OF THE SAME

CROSS-REFERENCE TO RELATED APPLICATIONS

This application claims the benefit of Korean Patent Application No. 10-2012-0083513, filed on Jul. 30, 2012, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 29,029 Byte ASCII (Text) file named "713928-ST25-2nd.txt" created on Oct. 14, 2013.

BACKGROUND

1. Field

The present disclosure relates to butyraldehyde dehydrogenases, which are improved for efficient production of 1,4-BDO, and transformed strains containing the same, and methods of producing high-efficiency 1,4-BDO by using the transformed microorganism.

2. Description of the Related Art 1,4-Butanediol (1,4-BDO), as a solvent used annually about 130 million tons worldwide, is produced from petroleum-based substances such as acetylene, butane, propylene, and butadiene.

1,4-BDO is used throughout the chemical industry as a polymer, a solvent, or a fine chemical intermediate of a variety of chemicals. Currently, most chemical substances composed of 4 carbon atoms are derived from 1,4-BDO, maleic anhydride, or the like and are synthesized. However, as oil prices are increasing, the cost of production is also increasing, bringing attention to develop a complementary and an alternative process of chemical production. Herein, a biological process using a microorganism is presented as an alternative to the chemical production process.

Unlike the existing chemical methods, Genometica built a biosynthetic pathway of 1,4-BDO in 2011 by using succinyl-CoA synthetase gene (sucCD) from *Clostridium kluyveri*, CoA-dependent succinate semialdehyde dehydrogenase gene (sucD) from *Porphyromonas gingivalis*, NAD dependent 4-hydroxybutyrate dehydrogenase gene (4hbd) from *P. gingivalis*, 4-hydroxybutyryl CoA:acetyl-CoA transferase gene (cat2) from *P. gingivalis*, and alcohol dehydrogenase gene (adhE2) from *Clostridium acetobutylicum* within *Escherichia coli* (*E. coli*).

According to an embodiment, pathways that are already identified in *E. coli* are modified to construct a new biosynthetic pathway. For example, a microorganism is developed for efficient production of 1,4-BDO with a Bld mutant that is appropriate for the new pathway.

SUMMARY

Provided are recombinant butyraldehyde dehydrogenases (Blds) used to produce high-efficiency 1,4-BDO. In particular, provided is an isolated polypeptide comprising the amino acid sequence of SEQ ID NO: 1 or a variant thereof comprising a substitution of at least one amino acid selected from the group consisting of Asn409, Arg361, Ala467, Met371, Ala176, Leu273, and Lys279 in the amino acid sequence of SEQ ID NO: 1, wherein the polypeptide catalyzes the conversion of 4-hydroxybutyryl CoA to 4-hydroxybutyraldehyde.

Provided are transformed (recombinant) microorganisms comprising polynucleotides encoding the recombinant Bld to produce high-efficiency 1,4-BDO.

Provided are transformed microorganisms comprising polynucleotides encoding the recombinant Bld and butanol dehydrogenase (Bdh) for use in producing high-efficiency 1,4-BDO.

Provided are transformed microorganisms comprising polynucleotides encoding sucCD, sucD, 4hbd, cat2, recombinant Bld, and bdh for use in producing high-efficiency 1,4-BDO.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which:

FIG. 2 is an absorbance graph obtained at a wavelength of 540 nm after 1 hour of the reaction. A BLD with a good activity results in the production of a lot of 4-hydroxybutyraldehydes, which is confirmed to be useful in a screening method. Bld-WT: pSTV-cs4c+pUCM-bld(WT), Bld-M1: pSTV-cs4c+pUCM-bldM1, Bld-M2: pSTV-cs4c+pUCM-bldM2, Bld-M3: pSTV-cs4c+pUCM-bldM3, Bld-M4: pSTV-cs4c+pUCM-bldM4, Bld-M5: pSTV-cs4c+pUCM-bldM5.

FIG. 5 is a comparison of butyraldehyde dehydrogenase (SEQ ID NO: 15) with sequences of proteins (3K9D corresponds to SEQ ID NO: 16 and 3MY7 corresponds to SEQ ID NO: 17) that are predicted to have a similar activity with the butyraldehyde dehydrogenase. Dark gray: this column of the alignment contains identical amino acid residues in all sequences (or identical bases if DNA sequences are aligned). Gray: this column of the alignment contains different but highly conserved (very similar) amino acids. Light gray: this column of the alignment contains different amino acids that are somewhat similar. Blank: this column of the alignment contains dissimilar amino acids or gaps (or different bases if DNA sequences are aligned).

FIG. 6A shows the three-dimensional structure of the whole Bld, and FIG. 6B shows a catalytic site of the Bld, and its substrate, NADPH.

DETAILED DESCRIPTION

Figure 1:
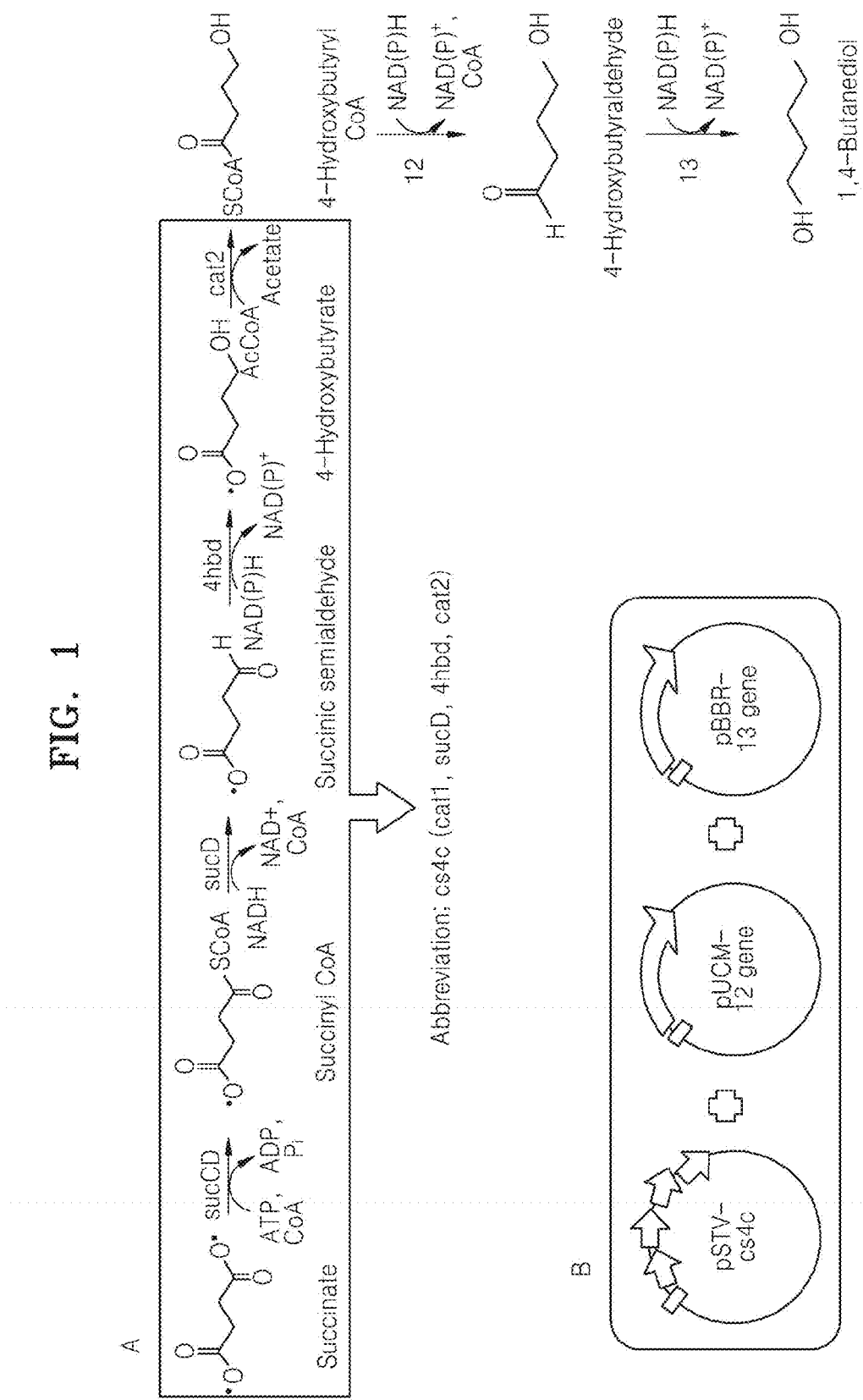
FIG. 1A depicts a biosynthetic pathway of 1,4-BDO built in *E. coli*.
FIG. 1B is a schematic diagram of vectors that are introduced in *E. coli*.

One aspect of the present invention provides a recombinant butyraldehyde dehydrogenase (Bld).

According to an aspect of the prevention invention, a butyraldehyde dehydrogenase or a butyraldehyde dehydrogenase mutant having a catalytic activity of converting 4-hydroxybutyryl CoA into 4-hydroxybutyraldehyde is provided.

The bld is a gene derived from *Clostridium saccharoperbutylacetonicum*. The Bld may have a polypeptide comprising the amino acid sequence of SEQ ID NO: 1.

The term "polynucleotide" used in the specification comprehensively refers to DNA (gNDA and cDNA) and RNA molecules. A nucleotide, the basic building unit in a polynucleotide, includes not only a natural nucleotide, but also an analogue wherein glucose or a base is transformed.

Herein, the butyraldehyde dehydrogenase mutant may have a substitution of at least one (e.g., 1, 2, 3, 4, 5, 6, or 7) amino acid selected from the group consisting of Asn409, Arg361, Ala467, Met371, Ala176, Leu273, and Lys279 in the amino acid sequence of SEQ ID NO: 1.

For example, the butyraldehyde dehydrogenase mutant may have a substitution as detailed below:

Asn409 with Thr, Arg361 with Ser, and Ala467 with Ser, in the amino acid sequence of SEQ ID NO: 1;

Arg361 with Ser and Ala467 with Ser in the amino acid sequence of SEQ ID NO: 1;

Met371 with Arg, Arg361 with Ser, and Ala467 with Ser in the amino acid sequence of SEQ ID NO:1;

Ala176 with Thr, Leu273 with Ile, Lys279 with Arg, Arg361 with Ser, and Ala467 with Ser in the amino acid sequence of SEQ ID NO: 1;

Ala176 with Thr in the amino acid sequence of SEQ ID NO: 1;

Leu273 with Ile in the amino acid sequence of SEQ ID NO: 1;

Lys279 with Arg in the amino acid sequence of SEQ ID NO: 1;

Arg361 with Ser in the amino acid sequence of SEQ ID NO: 1;

Ala467 with Ser in the amino acid sequence of SEQ ID NO: 1;

Asn409 with Thr in the amino acid sequence of SEQ ID NO: 1; and/or

Met371 with Arg in the amino acid sequence of SEQ ID NO: 1.

Also, the catalytic site of the mutant may have a substitution of at least one (e.g., 1, 2, 3, 4, 5, 6, 7, 8, 9, 10, 11, 12, 13, 14, 15, or 16) amino acid selected from the group consisting of Thr43, Asn144, Ala241, Gly242, Ala243, Gly244, Pro246, Leu273, Pro274, Ile276, Ala277, Lys279, Glu368, His398, Val432, and Thr441 in the amino acid sequence of SEQ ID NO: 1.

For example, the catalytic site of the mutant may have a substitution of Thr43 with Asp, Asn144 with Asp, Ala241 with Val, Gly242 with Ser, Ala243 with Gly, Gly244 with Ser, Pro246 with Tyr, Leu273 with Ile, Pro274 with Tyr, Ile276 with Leu, Ala277 with Val, Lys279 with Arg, Glu368 with Gln, His398 with Lys, Val432 with Leu, and Thr441 with Asp in the amino acid sequence of SEQ ID NO: 1.

Also, the mutant may have a substitution of at least one amino acid selected from the group consisting of Met91, Ile139, Thr140, Pro141, Ser142, Thr143, Asn166, Gly167, His168, Pro169, Gly170, Asn201, Pro202, Thr203, Met204, Leu207, Asp208, Ile210, Lle211, Lys212, Thr222, Gly223, Gly224, Pro225, Met227, Thr230, Leu231, Ala241, Gly242, Ala243, Gly244, Leu273, Pro274, Cys275, Ser326, Ile327, Asn328, Lys329, Val332, Thr367, Glu368, Leu369, Met370, and Arg396 in the amino acid sequence of SEQ ID NO: 1.

For example, the mutant may have a substitution of Met91 with Asp, Ile139 with Leu, Thr140 with Lys, Pro141 with Tyr, Ser142 with Gly, Thr143 with Lys, Asn166 with Asp, Gly167 with Ser, His168 with Lys, Pro169 with Tyr, Gly170 with Ser, Asn201 with Asp, Pro202 with Tyr, Thr203 with Lys, Met204 with Asp, Leu207 with Ile, Asp208 with Asn, Ile210 with Leu, Ile211 with Leu, Lys212 with Thr, Thr222 with Lys, Gly223 with Ser, Gly224 with Ser, Pro225 with His, Met227 with Lys, Thr230 with Lys, Leu231 with Val, Ala241 with Val, Gly242 with Ser, Ala243 with Val, Gly244 with Ser, Leu273 with Ile, Pro274 with His, Cys275 with Met, Ser326 with Gly, Ile327 with Leu, Asn328 with Asp, Lys329 with Thr, Val-332 with Leu, Thr367 with Lys, Glu368 with Gln, Leu369 with Ile, Met370 with Lys, and Arg396 with Lys in the amino acid sequence of SEQ ID NO: 1.

Thus, provided is an isolated polypeptide comprising the amino acid sequence of SEQ ID NO: 1 with a substitution of at least one amino acid selected from the group consisting of Asn409, Arg361, Ala467, Met371, Ala176, Leu273, and Lys279 in the amino acid sequence of SEQ ID NO: 1 and, optionally, (a) a substitution of at least one amino acid selected from the group consisting of Thr43, Asn144, Ala241, Gly242, Ala243, Gly244, Pro246, Leu273, Pro274, Ile276, Ala277, Lys279, Glu368, His398, Val432, and Thr441 in the amino acid sequence of SEQ ID NO: 1 and/or (b) a substitution of at least one amino acid selected from a group consisting of Met91, Ile139, Thr140, Pro141, Ser142, Thr143, Asn166, Gly167, His168, Pro169, Gly170, Asn201, Pro202, Thr203, Met204, Leu207, Asp208, Lle210, Lle211, Lys212, Thr222, Gly223, Gly224, Pro225, Met227, Thr230, Leu231, Ala241, Gly242, Ala243, Gly244, Leu273, Pro274, Cys275, Ser326, Ile327, Asn328, Lys329, Val332, Thr367, Glu368, Leu369, Met370, and Arg396 in the amino acid sequence of SEQ ID NO: 1.

In one embodiment, the butyraldehyde dehydrogenase mutant may be a polypeptide having a sequence set forth in the amino acid sequence of SEQ ID NO: 2, which is a variant of SEQ ID NO: 1 in which Leu273 has been substituted with Ile.

According to another aspect of the present invention, a polynucleotide that encodes the butyraldehyde dehydrogenase or butyraldehyde dehydrogenase mutant is provided. Herein, the polynucleotide may be derived from *Clostridium saccharoperbutylacetonicum*.

According to another aspect of the present invention, a recombinant microorganism that comprises the above-described polynucleotide and is capable of producing 1,4-BDO is provided.

The recombinant microorganism may further include a polynucleotide encoding butanol dehydrogenase (Bdh) having a catalytic activity of converting 4-hydroxybutyraldehyde into 1,4-butanediol. Herein, polynucleotide encoding bdh may comprise the nucleic acid sequence of SEQ ID NO: 18.

The recombinant microorganism may further include a polynucleotide encoding succinyl-CoA:coenzyme A transferase that converts succinate into succinyl CoA, a polynucleotide encoding CoA-dependent succinate semialdehyde dehydrogenase (SucD) that converts succinyl CoA into succinic semialdehyde, a polynucleotide encoding 4-hydroxybutyrate dehydrogenase (4Hbd) that converts succinic semialdehyde into 4-hydroxybutyrate, and a polynucleotide encoding 4-hydroxybutyryl CoA:acetyl-CoA transferase (Cat2) that converts 4-hydroxybutyrate into 4-hydroxybutyl CoA. In one embodiment, the microorganism may be *E. coli* (see, e.g., Yim et al., *Nat. Chem. Biol.*, 7(7): 445-452 (2011).

Also, a recombinant vector (e.g., expression vector) comprising a polynucleotide that encodes the recombinant Bld is provided.

The term "vector" refers to a DNA composite including DNA sequences operably connected with appropriate regulatory sequences that are capable of expressing DNA within an appropriate host. The vector may be a plasmid vector, a bacteriophage vector, a cosmid vector, a viral vector, or the like.

The vector (e.g., expression vector) can comprise a replication origin, a promoter, a multiple cloning site (MCS), and/or a selection marker. A replication origin enables a plasmid to replicate separately from a chromosome of a host. A promoter functions in the process of transcription of an inserted foreign gene. A MCS enables a foreign gene to be inserted via various restriction enzyme sites, and a selection marker confirms that a vector is properly inserted in a host cell. A selection marker includes antibiotic resistance genes that are commonly used in the art. Examples of the resistance genes are genes that are resistant to ampicillin, gentamicin, carbenicillin, chloramphenicol, streptomycin, kanamycin, geneticin, neomycin, and tetracycline. For example, in consideration of costs, the resistance genes may be genes that are resistant to ampicillin or gentamicin.

When the vector according to the present invention has a prokaryotic cell as a host, the vector may include a strong promoter, such as lambda PL promoter, trp promoter, lac promoter, T7 promoter, or the like. Meanwhile, when the vector has a eukaryotic cell as a host, the vector may include a promoter derived from the genome of mammalian cells (e.g., metallothionein) or a promoter derived from mammalian viruses (e.g., adenovirus late promoter, Vaccinia virus 7.5K promoter, SV40 promoter, cytomegalovirus promoter, and tk promoter of HSV). Exemplary promoters include the lambda PL promoter, trp promoter, lac promoter, or T7 promoter. Such promoters preferably are operably connected (i.e., linked) with foreign polynucleotide sequences (genes or cDNA) that encode a proteins of interest (e.g., Bld or mutants thereof).

The term "operably connected' refers to a functional connection between nucleic acid expression regulatory sequences (e.g., a promoter, a signal sequence, or an array on a transcription regulatory factor-binding site) and other nucleic acid sequences. Due to the operable connection, the regulatory sequences regulate a transcription and/or a translation of the nucleic acid sequences that encode the proteins of interest (e.g., Bld or mutants thereof).

According to another aspect of the present invention, a method of producing 4-hydroxybutyaldehyde includes contacting 4-hydroxybutyryl CoA with butyraldehyde dehydrogenase or a butyraldehyde dehydrogenase mutant. The butyraldehyde dehydrogenase or butyraldehyde dehydrogenase mutant may comprise, consist essentially of, or consist of the amino acid sequences of SEQ ID NO: 1 or 2, respectively.

According to another aspect of the present invention, a method of producing an 1,4-butanediol includes contacting a 4-hydroxybutyaldehyde with butanol dehydrogenase, thereby producing 1,4-butanediol. The Bdh may be encoded by the nucleic acid sequence of SEQ ID NO: 18.

According to another aspect of the present invention, a method of producing 1,4-BDO includes contacting 4-hydroxybutyryl CoA with Bld or a Bld mutant; and contacting the resultant reaction product with a bdh, thereby producing 1,4-BDO.

According to another aspect of the present invention, a method of producing 1,4-BDO includes introducing butyraldehyde dehydrogenase or a butyraldehyde dehydrogenase mutant, and a bdh to a microorganism; incubating the microorganism; and separating 1,4-BDO from the microorganism, is provided.

In each of the above-described methods, the butyraldehyde dehydrogenase, butyraldehyde dehydrogenase mutant, and/or bdh may be introduced as a polynucleotide (e.g., cDNA or vector) or polypeptide.

Available carbon sources that the microorganism may use may be monosaccharide, disaccharide, polysaccharide, or the like. For example, glucose, fructose, mannose, galactose, or the like may be used. Also, available nitrogen sources that the microorganism may use may be organic nitrogen compounds, inorganic nitrogen compounds, or the like. For example, amino acids, amides, amines, nitrates, ammonium salts, or the like may be used. An oxygen condition for incubating a microorganism may be an aerobic condition of normal oxygen partial pressure, a hypoxic condition containing 0.1~10% oxygen in the atmosphere, or an oxygen-free anaerobic condition.

The introduction steps of the above-described methods may include further introducing a polynucleotide (e.g., gene or cDNA) encoding sucCD that converts succinate into succinyl CoA, a polynucleotide (e.g., gene or cDNA) encoding sucD that converts succinyl CoA into succinic semialdehyde, a polynucleotide (e.g., gene or cDNA) encoding 4hbd that converts succinic semialdehyde into 4-hydroxybutyrate, and a polynucleotide (e.g., gene or cDNA) encoding cat2 that converts 4-hydroxybutyrate into 4-hydroxybutyl CoA.

According to another aspect of the present invention, a method of confirming the yield of 1,4-BDO comprises introducing Bld or a Bld mutant to a microorganism; contacting the microorganism with Schiff's reagent; and measuring absorbance. Herein, the confirmation of the yield of 1,4-BDO yield is performed by measurement of the yield of 4-hydroxybutyraldehyde.

EXAMPLES

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Example 1

Transgenic Host and Manufactured Expression Vector for Transformation

Recombinant microorganisms used to efficiently product 1,4-BDO and expression vectors used to transform the microorganisms are shown in Table 1 below.

TABLE 1

| Strains and plasmids | Relevant properties | Source or reference |
|---|---|---|
| Strains | | |
| *Escherichia coli* XL1-Blue | F'::Tn10 proA+B+ laclq Δ(lacZ)M15/recA1 endA1 gyrA96 (Nalr) thihsdR17 (rK mK+) glnV44 relA1 lac | Stratagene |
| *Escherichia coli* TOP10 | F-mcrA Δ(mrr-hsdRMS-mcrBC) φ80lacZΔM15 ΔlacX74 nupG recA1 araD139 Δ(ara-leu)7697 galE15 galK16 rpsL(Str$^R$)endA1 | Invitrogen |
| *Clostridium saccharoperbutylacetonicum* KCTC 5577 | Source for bld and bdh genes | KCTC |
| *Clostridium acetobutylicum* KTCT1790 | Source for adhE2 gene | KCTC |
| Plasmids | | |
| pUCM | Cloning vector modified from pUC19; constitutive lac promoter, Ap$^r$ | 1 |
| pUCM-bld | Constitutively expressed bld gene of *C. saccharoperbutylacetonicum* | This study |
| pUCM-adhE2 | Constitutively expressed adhE2 gene from *C. acetobutylicum* | This study |
| pUCM-bdh | Constitutively expressed bdh gene of *C. saccharoperbutylacetonicum* | This study |
| pUCM-bld-M1-5 series | Constitutively expressed bld mutant genes 1-5 generated by random mutagenesis | This study |
| pUCM-bld-S1-6 series | Constitutively expressed bld mutant genes 1-6 generated by site-directed mutagenesis | This study |
| pBBR1MCS2 | Broad-host-range plasmid, Km$^r$ | 2 |
| pBBR-bdh | Constitutively expressed bdh gene of *C. saccharoperbutylacetonicum*, Km$^r$ | This study |
| pSTV28 | Plasmid with a replication origin of pACYC184, Cm$^r$ | Takara |
| pSTV-cs4c | Constitutively expressed sucCD, sucD, 4hbd, and cat2 genes together | This study |

1. Kim, S. H., Y. H. Park, C. Schmidt-Dannert, and P. C. Lee. 2010. Redesign, reconstruction, and directed extension of the brevibacterium linens C40 carotenoid pathway in *escherichia coli*. Applied and Environmental Microbiology 76: 5199-5206.
2. Peterson, K. M. 1995. Four new derivatives of the broad-host-range cloning vector pBBR1MCS, carrying different antibiotic-resistance cassettes. Gene 166: 175-176.

Example 2

Modularization of Biosynthetic Pathway Genes sucCD-sucD-4hbd-cat2 genes synthesized in a pGEM vector were cloned at positions of Xba I and Not I of a pUCM vector with a constitutive promoter. Then, subcloning was performed at positions of Sac I and BamH I of a pSTV 28 vector.

AdhE2 was amplified in *Clostridium acetobutylicum*'s chromosomal DNA by PCR, and then, cloning was performed at positions of Xba I and Not I of pUCM vector. PCR was performed by using DNA engine thermal cycler (Bio-Rad), for 4 minutes at the temperature of 95° C., following by 1 minute at the temperature of 94° C., 40 seconds at the temperature of 50° C., and 1 minute at the temperature of 72° C., and the latter three processes were repeatedly performed 32 times. Finally the PCR was further performed at the temperature of 72° C. for 7 minutes.

DNA sequences for each primer are shown in Table 2 below.

TABLE 2

| Gene site | Sequence | SEQ ID NO | Enzyme |
|---|---|---|---|
| bdh | F; 5'-GCTCTAGAAGGAGGATTACAAAATGGAGAATTTTAGATTTAATG-3' | 3 | Xba I |
| bdh | R; 5'-TTCCCTTGCGGCCGCTTAAAGGGACATTTCTAA-3' | 4 | Not I |
| bld | F; 5'-GCCCCGGGAGGAGGATTACAAAATGATTAAAGACACGCTAGTTTC-3' | 5 | Xma I |
| bld | R; 5'-TTCCCTTGCGGCCGCTTAACCGGCGAGTACACATC-3' | 6 | Not I |
| cs4c | F; 5'-GCTCTAGAAGGAGGATTACAAAATGAGTAAAGGATTAAGAAC-3' | 7 | Xba I |
| cs4c | R; 5'-TTCCCTTGCGGCCGCTTAACCAAAACGTTTGCG-3' | 8 | Not I |
| Sub_BamHI_R | R; 5'-CGGGATCCCGGTGTGAAATACCG-3' | 9 | BamH I |

TABLE 2-continued

| Gene site | Sequence | SEQ ID NO | Enzyme |
|---|---|---|---|
| Sub_EcoRI_R | R; 5'-GAATTCCGGTGTGAAATACCG-3' | 10 | EcoR I |
| Sub_SacI_F | F; 5'-GAGCTCCCGACTGGAAAGCG-3' | 11 | Sac I |
| Sub_SalI_F | F; 5'-ACGCGTCGACCCGACTGGAAAGCG-3' | 12 | Sal I |
| adhE2 | F; 5'-GCTCTAGAAGGAGGATTACAAAATGATTTTGCATCTGCTG-3' R; | 13 | Xba I |
|  | 5'-TTCCCTTGCGGCCGCTTAAAACGACTTGATGTAGAT-3' | 14 | Not I |

Example 3

Genetic Improvement and Screening

<3-1> Manufacture of Bld Mutants

A bld gene was transformed by directed evolution to increase the production of 1,4-BDO. Sequences of the bld gene were changed by error prone PCR. In this regard, 2.5 mM $MgCl_2$ and a subcloning primer were used. By using G-rich dNTP (T:A:C:G=1:1:1:4) and T-rich dNTP (T:A:C:G=4:1:1:1) separately, a variety of errors were increased. These bld mutants were inserted at positions of Xma I and Not I of a pUCM vector to produce pUCM-bld.

<3-2> Screening of Bld Mutants for Highly Efficient Production of 1,4-BDO pUCM-bld was introduced to TOP10 to which the pSTV 28-sucCD-sucD-4hbd-cat2 (pSTV-cs4c) vector was introduced.

Figure 2:
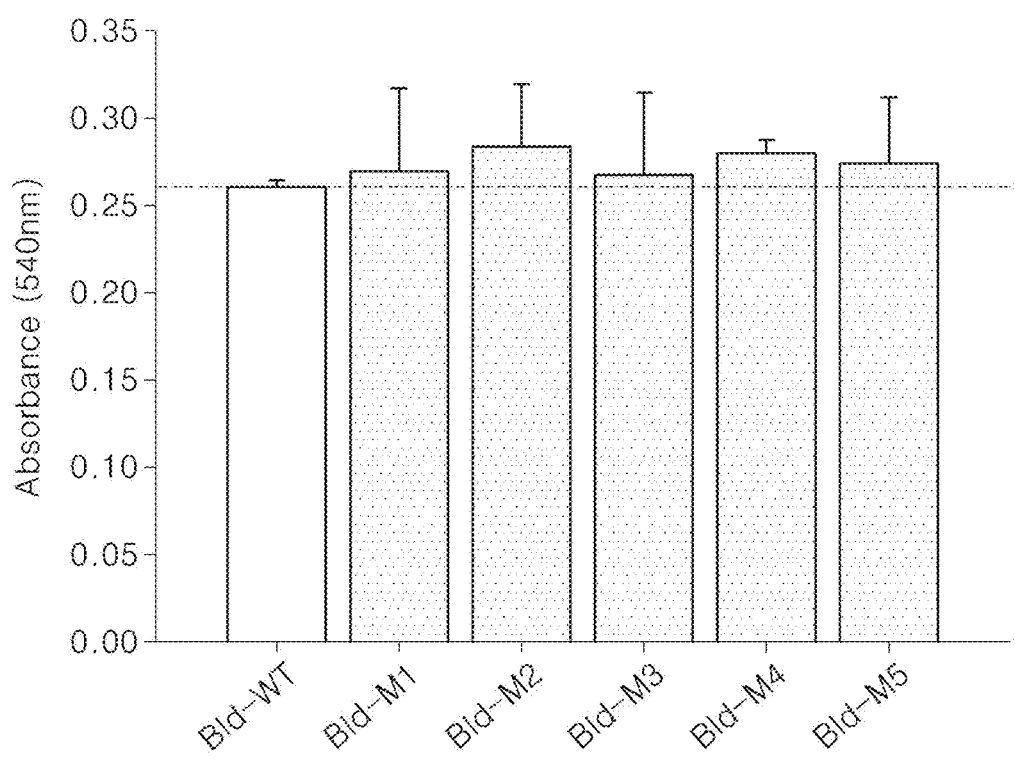
FIG. 2 shows the results of an aldehyde reaction when the supernatant obtained by incubating selected colonies reacts with Schiff's reagent.

Schiff's reagent was used to search for a bld mutant that is capable of increasing the yield among libraries. Schiff's reagent was a solution including 30 mg/ml sodium bisulfate (in water), 0.5 M KCl (in water), and 2 mg/ml pararosaniline (in ethanol) which were mixed at a ratio of 2:1:2, and the solution was added to 0.8% agar (in water) for reaction on a plate with colonies floating thereon. After mixing the two solutions, the mixture was poured onto a plate and a reaction was performed at 37° C. for 3 hours. Then, red colonies were selected and incubated on 2 ml LB culture under the conditions of 37° C., 250 rpm, and 12 hours. 200 µl of the supernatant (obtained by centrifuging 1 ml of the culture medium at 13,000 rpm for 10 minutes) and 100 µl of Schiff's reagent were mixed together and reacted at 37° C. for about 1 to 5 hours. Absorbance was measured at 540 nm. Colonies showing high absorbance were introduced to TOP 10 along with pSTV-cs4c and pBBR-bdh and incubated (see FIG. 2).

Example 4

E. coli Incubation and 1,4-BDO Production

E. coli strain TOP10 was used to produce 1,4-BDO by the cloning and expression of the gene modules.

Recombinant E. coli including 3 plasmids (pSTV-cs4c, pBBR-bdh, and pUCM-bld) were incubated using a serum bottle under anaerobic conditions of 30° C., 250 rpm, and 48 hours. The medium composition was 100 ml of LB containing 0.6% calcium carbonate and 2% glucose, and 50 µg/ml chloramphenicol, 100 µg/ml ampicillin, and 50 µg/ml kanamycin were all added thereto.

An incubation condition was prepared as an anaerobic condition by injecting nitrogen and the incubation was performed at 30° C., 250 rpm, and 18 hours. The medium composition was 1 L of LB medium including 2% glucose, and 50 µg/ml chloramphenicol, 100 µg/ml ampicillin, and 50 µg/ml kanamycin were all added thereto.

When the modulated genes that were associated with biosynthesis of 1,4-BDO were transformed within E. coli by the method mentioned above, the recombinant E. coli produced 1,4-BDO. However, less 1,4-BDO was produced since 4-hydroxybutyrate accumulated first. Therefore, experiments were designed in a way that 4-hydroxybutyraldehydes were produced in great quantities to make a biosynthetic pathway towards 1,4-BDO.

Example 5

Analysis of 1,4-BDO 1 ml of 100 ml culture obtained in Example 4 was extracted and centrifuged at 13000 rpm for 30 minutes, and the supernatant was centrifuged again under the same condition. Then 800 µl was filtered through a 0.45 um filter to prepare a sample. 10 µl of the sample was used for HPLC analysis. HPLC was performed by using Agilent 1100 device equipped with Refractive index detector (RID). 4 mM $H_2SO_4$ solution was used as a mobile phase and BIO-RAD Aminex HPX-87H Column was used as a stationary phase wherein the flow rate is 0.7 ml/min. Temperature of the column and detector was both 50° C.

Figure 3:
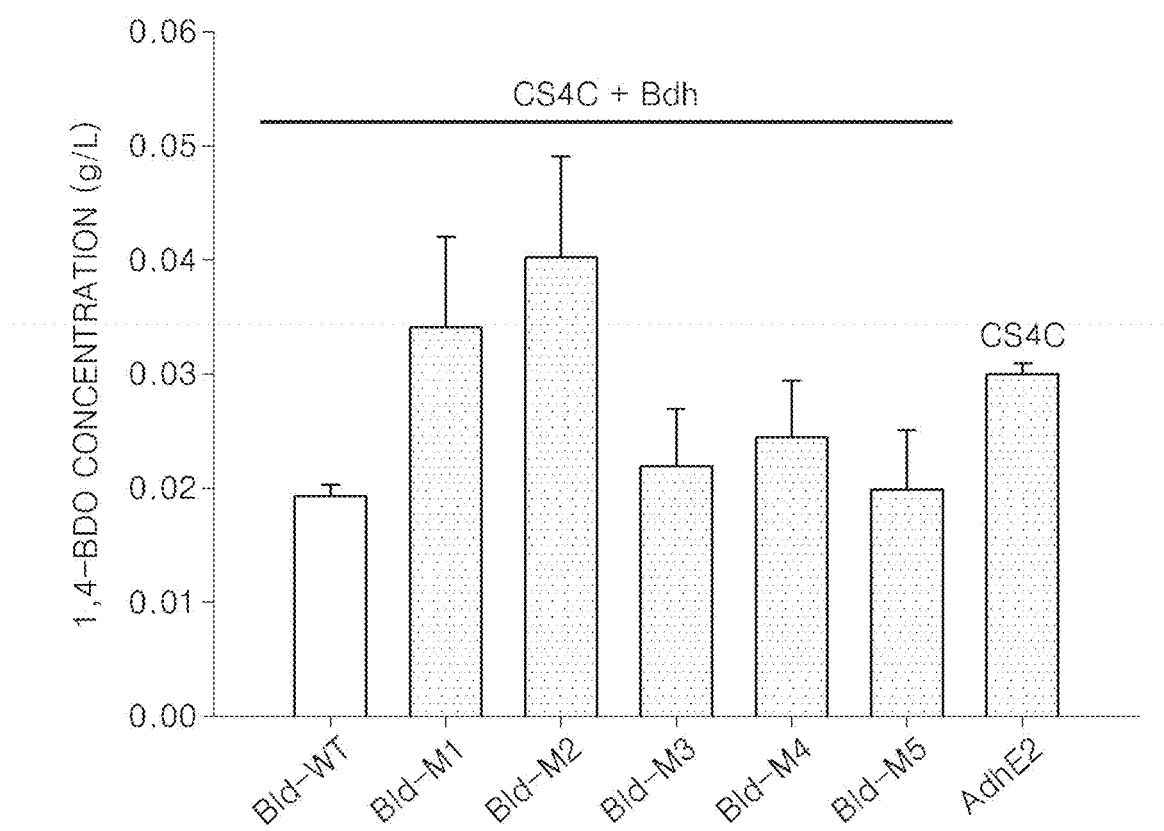
FIG. 3 is a graph showing the yield of 1,4-BDO from a Bld mutant produced by introducing cs4c (sucCD, sucD, 4hbd, and cat2 genes) and a bdh to Bld-WT and various Bld mutants (Bld-M1 to Bld-M5) in a microorganism. As a positive control, cs4c and adhE were introduced to a microorganism and the yield of 1,4-BDO was determined.

The yield of 1,4-BDO was analyzed and results show that more 1,4-BDO was produced when the mutant bld was introduced and incubated than when the existing Bld was expressed with cs4c and bdh genes within TOP10. The Bld-M2 sample produced about 0.04 g/L concentration of 1,4-BDO, more than twice compared to others (see FIG. 3). Bld-M1, Bld-M3, Bld-M4, and Bld-M5 samples also showed higher 1,4-BDO productivity than the control (Bld-WT) (see FIG. 3). As a result of analyzing nucleotide sequences of the Bld mutants, the sequences were identified as shown in Table 3.

From the results above, it was confirmed that when the butyraldehyde dehydrogenase has high activity, more 4-hydroxybutyraldehyde was produced, and the hydroxybutyraldehyde bound to Schiff's reagent to produce color, which is useful for screening.

TABLE 3

| Mutant | Nucleotide Mutation | Amino Acid Mutation |
|---|---|---|
| Bld-M1 | AAC → ACC | N409T |
|  | AGG → AGT | R361S |
|  | GCC → TCC | A467S |
| Bld-M2 | AGG → AGT | R361S |
| Bld-M3 | AGG → AGT | R361S |
|  | GCC → TCC | A467S |
| Bld-M4 | AGG → AGT | R361S |
|  | ATG → AGG | M371R |
|  | GCC → TCC | A467S |

TABLE 3-continued

| Mutant | Nucleotide Mutation | Amino Acid Mutation |
|---|---|---|
| Bld-M5 | GCT → ACT | A176T |
| | TTA → ATA | L273I |
| | AAA → AGA | K279R |
| | AGG → AGT | R361S |
| | GCC → TCC | A467S |
| Bld-S1 | GCT → ACT | A176T |
| Bld-S2 | TTA → ATA | L273I |
| Bld-S3 | AAA → AGA | K279R |
| Bld-S4 | ATG → AGG | M371R |
| Bld-S5 | AAC → ACC | N409T |
| Bld-S6 | GCC → TCC | A467S |

Example 6

Screening the Most Effective Bld Mutant

Figure 4:
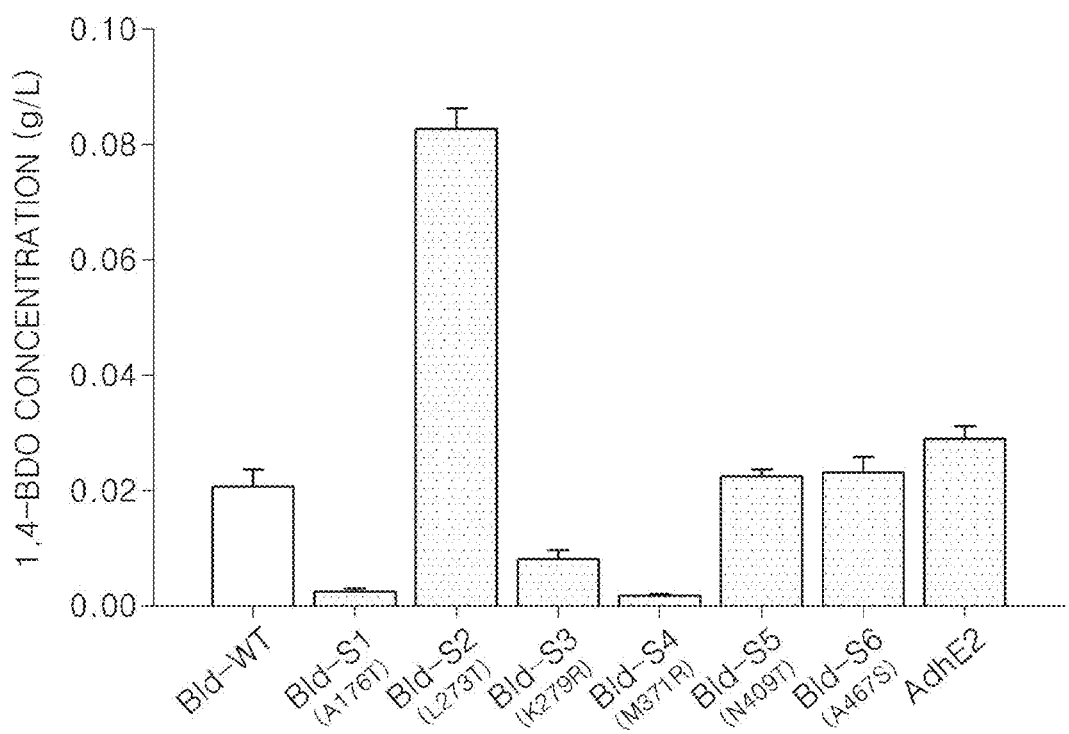
FIG. 4 is a graph that illustrates which mutation position selected from Bld-M1 to Bld-M5 (shown in Table 3) induces an activity of the butyraldehyde dehydrogenase mutant the most. Bld-S1 to Bld-S6 mutants were produced, and the yield of 1,4-BDO was confirmed by using the produced butyraldehyde dehydrogenase mutants. As a result, it was confirmed that 1,4-BDO was substantially produced in the case of Bld-S2 mutant, and a mutant having a substitution at the $273^{rd}$ position of Bld-WT (see SEQ ID NO: 1) had the most excellent 1,4-BDO productivity.

As shown in Table 3 above, the Bld-M1 to Bld-M5 mutants were confirmed to have from 1 to as many as 5 mutated amino acids. Herein, in order to find out which mutant was the most effective, yields of 1,4-BDO of a total 6 mutants were measured in the same manner as Examples 4 and 5. As shown in FIG. 4, a microorganism producing the Bld-S2 (L273I) mutant was confirmed to have the highest yield of 1,4-BDO (0.08 g/L). Other mutants (Bld-S5 and Bld-S6) also showed a slight improvement. Notably, Bld-S2 having the L273I mutation showed more than three times greater effects than adhE2, which is known to have the highest performance among others of this kind.

Example 7

Homology Modeling of Bld

Figure 5:
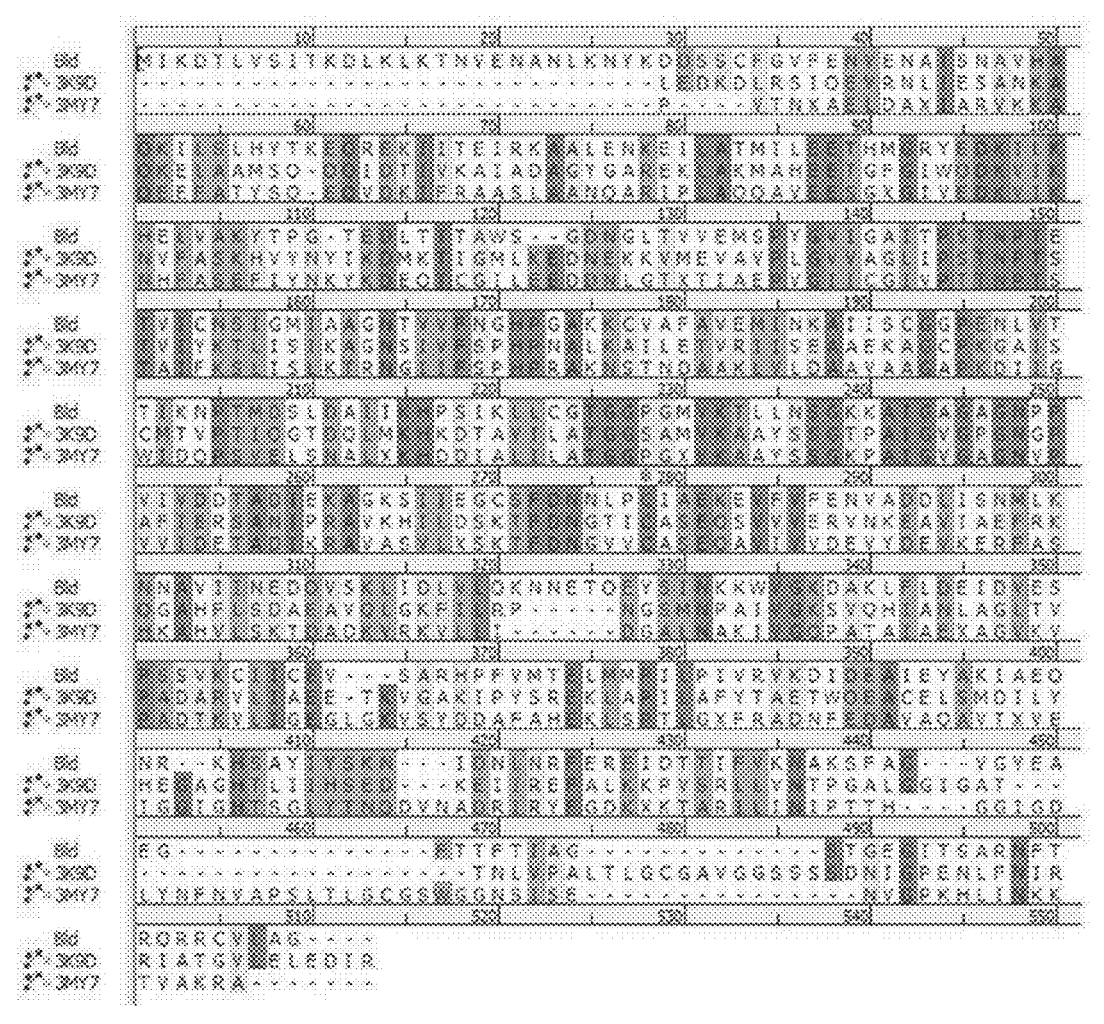

Revealing the effect of mutants on an activity of an enzyme requires identification of a three-dimensional structure of the enzyme. However, the three-dimensional structure of the Bld enzyme was not identified yet. Therefore, the three-dimensional structure of the Bld was newly created by using a method of homology modeling. First, a protein structure having similar sequences with the Bld enzyme was searched for, and as a result, two proteins (Protein Data Bank ID: 3K9D, 3MY7) having the highest similarity were identified. By using the sequences of these two proteins as a template, the sequences of the Bld enzyme were arranged in this template (FIG. 5). Finally, the template-based three dimensional structure of Bld was created (FIG. 6). All the modeling methods used Discovery Studio 3.1 software.

Figure 6A:
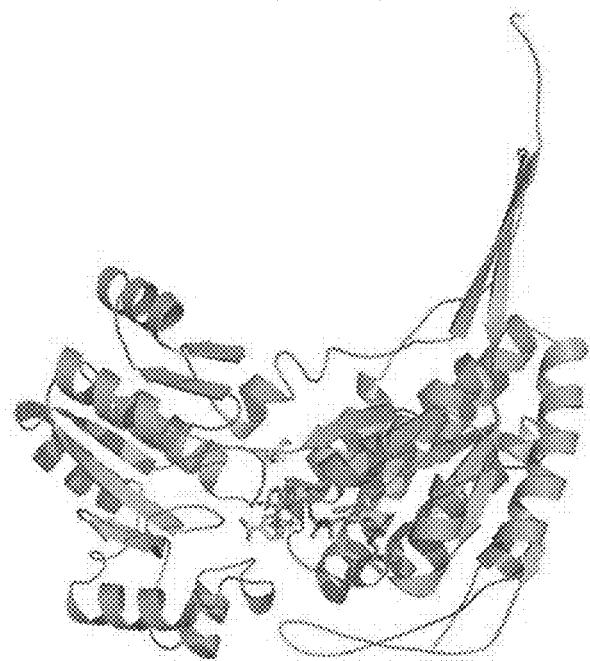
FIGS. 6A and 6B show a three-dimensional structure of the Bld.
Figure 6B:
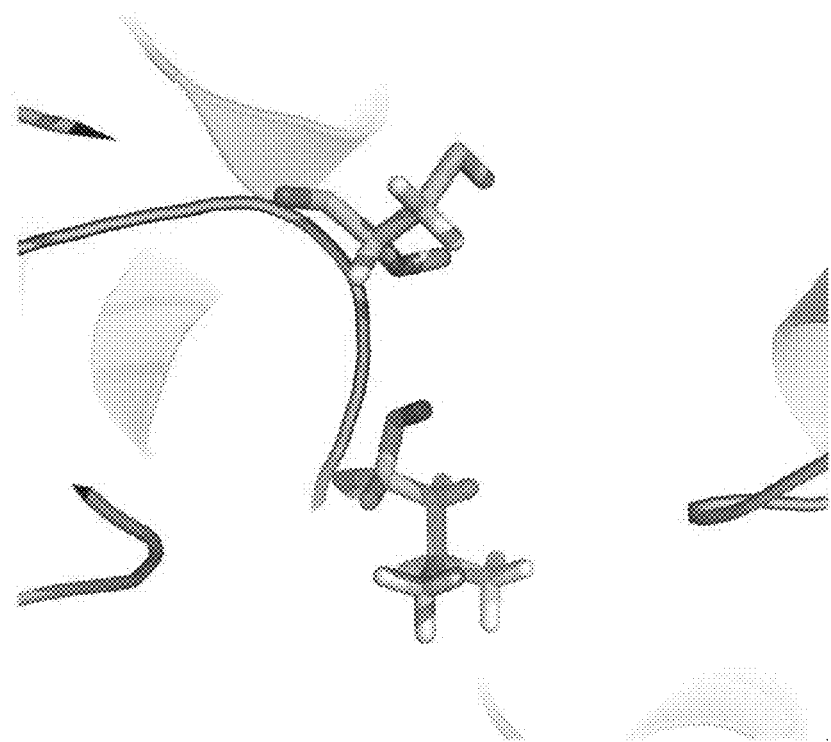

According to the reaction mechanism of aldehyde dehydrogenase, a substrate that reacts with amino acids exists, and this is well preserved as cysteine amino acid in various aldehyde dehydrogenases (see, e.g., J. Mol. Biol (2007) 366, 481-493; Nat. Struct. Mol. Biol. (1997) 4, 317-326). Through the sequence alignment results, the cysteine amino acid was confirmed to be preserved in the Bld enzyme as well, which is the 275$^{th}$ amino acid (Cys275) (FIG. 5). When analyzing the mutants that have an improved activity of the Bld based on the three-dimensional structure, the activity of the enzyme was shown to be increased when the mutation occurs near Cys275 or near the coenzyme binding site (FIGS. 6A-6B). FIG. 6A shows a three-dimensional structure of the Bld enzyme which is produced by homology modeling. Cys275 and Leu273 amino acids were illustrated as yellow stick models and the coenzyme was illustrated as a pink stick model. FIG. 6B is a close-up view of the catalytic site, and the coenzyme is not shown to reveal the location of the two amino acids described above better.

From these results, possibilities for the improvement of the Bld enzyme were confirmed by mutating amino acids near Cys275. Namely, it was confirmed that the transformation of amino acids near the catalytic site that reacts with a substrate contributes to the improvement of the activity of the corresponding enzyme.

When a new enzyme according to an embodiment of the present invention is used, 1,4-BDO productivity is increased. Accordingly, when the activity of the Bld enzyme is enhanced by directed evolution, this may be very usefully utilized in industry.

According to an embodiment of the present invention, 1,4-BDO productivity is confirmed by the expression performed by introducing bld and bdh to *E. coli* during the biosynthesis pathway of 1,4-BDO. In addition, a Bld mutant enabling high-efficiency production of is obtained, and by using the mutant, a recombinant transformed microorganism is obtained whose 1,4-BDO production concentration is improved more than twice than a conventional case. When the transformed microorganism is used, 1,4-BDO may be efficiently produced.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated polypeptide comprising a variant of the amino acid sequence of SEQ ID NO: 1, wherein the variant comprises at least one amino acid substitution selected from the group consisting of Asn409, Arg361, Ala467, Met371, Ala176, Leu273 and Lys279 in the amino acid sequence of SEQ ID NO: 1, wherein the polypeptide variant catalyzes the conversion of 4-hydroxybutyryl CoA to 4-hydroxybutyraldehyde.

2. The polypeptide of claim 1, wherein the polypeptide comprises a variant of SEQ ID NO: 1 comprising a substitution of Asn409 with Thr, Arg361 with Ser, and Ala467 with Ser in the amino acid sequence of SEQ ID NO: 1.

3. The polypeptide of claim 1, wherein the polypeptide comprises a variant of SEQ ID NO: 1 comprising a substitution of Arg361 with Ser, and Ala467 with Ser in the amino acid sequence of SEQ ID NO: 1.

4. The polypeptide of claim 1, wherein the polypeptide comprises a variant of SEQ ID NO: 1 comprising a substitution of "Met371 with Arg", Arg361 with Ser, and Ala467 with Ser in the amino acid sequence of SEQ ID NO: 1.

5. The polypeptide of claim 1, wherein the polypeptide comprises a variant of SEQ ID NO: 1 comprising a substitution of Ala176 with Thr, Leu273 with Ile, Lys279 with Arg, Arg361 with Ser, and Ala467 with Ser in the amino acid sequence of SEQ ID NO:1.

6. The polypeptide of claim 1, wherein the polypeptide comprises a variant of SEQ ID NO: 1 comprising a substitution of Ala176 with Thr in the amino acid sequence of SEQ ID NO: 1.

7. The polypeptide of claim 1, wherein the polypeptide comprises a variant of SEQ ID NO: 1 comprising a substitution of Leu273 with Ile in the amino acid sequence of SEQ ID NO: 1.

8. The polypeptide of claim 1, wherein the polypeptide comprises a variant of SEQ ID NO: 1 comprising a substitution of Lys279 with Arg in the amino acid sequence of SEQ ID NO: 1.

9. The polypeptide of claim 1, wherein the polypeptide comprises a variant of SEQ ID NO: 1 comprising a substitution of Arg361 with Ser in the amino acid sequence of SEQ ID NO: 1.

10. The polypeptide of claim 1, wherein the polypeptide comprises a variant of SEQ ID NO: 1 comprising a substitution of Ala467 with Ser in the amino acid sequence of SEQ ID NO: 1.

11. The polypeptide of claim 1, wherein the polypeptide comprises a variant of SEQ ID NO: 1 comprising a substitution of Asn409 with Thr in amino acid sequence of SEQ ID NO: 1.

12. The polypeptide of claim 1, wherein the polypeptide comprises a variant of SEQ ID NO: 1 comprising a substitution of Arg371 with Arg in the amino acid sequence of SEQ ID NO: 1.

13. The polypeptide of claim 1, wherein the polypeptide comprises a variant of SEQ ID NO: 1 comprising a substitution of at least one selected from a group consisting of Ala176 with Thr, Leu273 with Ile, Lys279 with Arg, Arg361 with Ser, Ala467 with Ser, Asn409 with Thr, and Arg371 with Ser in the SEQ ID NO: 1.

14. A recombinant microorganism that is capable of producing 1,4-BDO, the microorganism comprising the polypeptide of claim 1.

15. The microorganism of claim 14, further comprising a polynucleotide encoding butanol dehydrogenase that converts 4-hydroxybutyraldehydeto into 1,4-butanediol.

16. The microorganism of claim 15, further comprising a polynucleotide encoding succinyl-CoA:coenzyme A transferase that converts succinate into succinyl CoA, a polynucleotide encoding CoA-dependent succinate semialdehyde dehydrogenate that converts succinyl CoA into succinic semialdehyde, a polynucleotide encoding 4-hydroxybutyrate dehydrogenase that converts succinic semialdehyde into 4-hydroxybutyrate, and a polynucleotide encoding 4-hydroxybutyryl CoA:acetyl-CoA transferase that converts 4-hydroxybutyrate into 4-hydroxybutyl CoA.

17. A method of producing 4-hydroxybutyaldehyde, the method comprising: contacting 4-hydroxybutyryl CoA with the polypeptide of claim 1.

18. The method of claim 17, wherein the polypeptide of claim 1 comprises the amino acid sequence set forth in SEQ ID NO: 2.

19. A method of producing 1,4-BDO, the method comprising:
- incubating a microorganism comprising a polynucleotide encoding the polypeptide of claim 1 and a polynucleotide encoding butanol dehydrogenase with a carbon source; and
- separating 1,4-BDO from the microorganism.

20. The method of claim 19, further comprising introducing the polynucleotide encoding the polypeptide of claim 1, the polynucleotide encoding butanol dehydrogenase, or both, into the microorganism.

21. The method of claim 19, wherein the microorganism further comprises
- a polynucleotide encoding succinyl-CoA:coenzyme A transferase that converts succinate into succinyl CoA,
- a polynucleotide encoding CoA-dependent succinate semialdehyde dehydrogenate that converts succinyl CoA into succinic semialdehyde,
- a polynucleotide encoding 4-hydroxybutyrate dehydrogenase that converts succinic semialdehyde into 4-hydroxybutyrate, and
- a polynucleotide encoding 4-hydroxybutyryl CoA:acetyl-CoA transferase that converts 4-hydroxybutyrate into 4-hydroxybutyl CoA.

* * * * *

```
                        SEQUENCE LISTING

<160> NUMBER OF SEQ ID NOS: 19

<210> SEQ ID NO 1
<211> LENGTH: 468
<212> TYPE: PRT
<213> ORGANISM: Clostridium saccharoperbutylacetonicum

<400> SEQUENCE: 1

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
                20                  25                  30

Cys Phe Gly Val Phe Glu Asn Val Glu Asn Ala Ile Ser Asn Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335
```

```
Lys Leu Phe Leu Asp Glu Ile Asp Val Glu Ser Pro Ser Ser Val Lys
                340                 345                 350

Cys Ile Ile Cys Glu Val Ser Ala Arg His Pro Phe Val Met Thr Glu
            355                 360                 365

Leu Met Met Pro Ile Leu Pro Ile Val Arg Val Lys Asp Ile Asp Glu
        370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 2
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273I)

<400> SEQUENCE: 2

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
```

```
                210                 215                 220
Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
                260                 265                 270

Ile Pro Cys Ile Ala Glu Lys Glu Val Phe Val Phe Glu Asn Val Ala
                275                 280                 285

Asp Asp Leu Ile Ser Asn Met Leu Lys Asn Asn Ala Val Ile Ile Asn
                290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
                340                 345                 350

Cys Ile Ile Cys Glu Val Ser Ala Arg His Pro Phe Val Met Thr Glu
                355                 360                 365

Leu Met Met Pro Ile Leu Pro Ile Val Arg Val Lys Asp Ile Asp Glu
370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
                435                 440                 445

Gly Glu Gly Ile Thr Ser Ala Arg Asn Phe Thr Arg Gln Arg Arg Cys
                450                 455                 460

Val Leu Ala Gly
465

<210> SEQ ID NO 3
<211> LENGTH: 44
<212> TYPE: DNA
<213> ORGANISM: Artificial Sequence
<220> FEATURE:
<223> OTHER INFORMATION: Synthetic (forward primer of bdh)

<400> SEQUENCE: 3
gctctagaag gaggattaca aaatggagaa ttttagattt aatg                    44

<210> SEQ ID NO 4
<211> LENGTH: 33
<212> TYPE: DNA
<213> ORGANISM: Artificial Sequence
<220> FEATURE:
<223> OTHER INFORMATION: Synthetic (reverse primer of bdh)

<400> SEQUENCE: 4
ttcccttgcg gccgcttaaa gggacatttc taa                                33

<210> SEQ ID NO 5
<211> LENGTH: 45
<212> TYPE: DNA
<213> ORGANISM: Artificial Sequence
```

```
<220> FEATURE:
<223> OTHER INFORMATION: Synthetic (forward primer of bld)

<400> SEQUENCE: 5
gccccgggag gaggattaca aaatgattaa agacacgcta gtttc          45

<210> SEQ ID NO 6
<211> LENGTH: 35
<212> TYPE: DNA
<213> ORGANISM: Artificial Sequence
<220> FEATURE:
<223> OTHER INFORMATION: Synthetic (reverse primer of bld)

<400> SEQUENCE: 6
ttcccttgcg gccgcttaac cggcgagtac acatc                      35

<210> SEQ ID NO 7
<211> LENGTH: 43
<212> TYPE: DNA
<213> ORGANISM: Artificial Sequence
<220> FEATURE:
<223> OTHER INFORMATION: Synthetic (forward primer of cs4c)

<400> SEQUENCE: 7
gctctagaag gaggattaca aaatgagtaa agggattaag aac             43

<210> SEQ ID NO 8
<211> LENGTH: 33
<212> TYPE: DNA
<213> ORGANISM: Artificial Sequence
<220> FEATURE:
<223> OTHER INFORMATION: Synthetic (reverse primer of cs4c)

<400> SEQUENCE: 8
ttcccttgcg gccgcttaac caaaacgttt gcg                        33

<210> SEQ ID NO 9
<211> LENGTH: 23
<212> TYPE: DNA
<213> ORGANISM: Artificial Sequence
<220> FEATURE:
<223> OTHER INFORMATION: Synthetic (Sub_BamHI_R)

<400> SEQUENCE: 9
cgggatcccg gtgtgaaata ccg                                   23

<210> SEQ ID NO 10
<211> LENGTH: 23
<212> TYPE: DNA
<213> ORGANISM: Artificial Sequence
<220> FEATURE:
<223> OTHER INFORMATION: Synthetic (Sub_EcoRI_R)

<400> SEQUENCE: 10
cgggatcccg gtgtgaaata ccg                                   23

<210> SEQ ID NO 11
<211> LENGTH: 20
<212> TYPE: DNA
<213> ORGANISM: Artificial Sequence
<220> FEATURE:
<223> OTHER INFORMATION: Synthetic (Sub_SacI_F)

<400> SEQUENCE: 11
gagctcccga ctggaaagcg                                       20
```

<210> SEQ ID NO 12
<211> LENGTH: 24
<212> TYPE: DNA
<213> ORGANISM: Artificial Sequence
<220> FEATURE:
<223> OTHER INFORMATION: Synthetic (Sub_SalI_F)

<400> SEQUENCE: 12
acgcgtcgac ccgactggaa agcg                                              24

<210> SEQ ID NO 13
<211> LENGTH: 40
<212> TYPE: DNA
<213> ORGANISM: Artificial Sequence
<220> FEATURE:
<223> OTHER INFORMATION: Synthetic (forward primer of adhE2)

<400> SEQUENCE: 13
gctctagaag gaggattaca aaatgatttt gcatctgctg                              40

<210> SEQ ID NO 14
<211> LENGTH: 36
<212> TYPE: DNA
<213> ORGANISM: Artificial Sequence
<220> FEATURE:
<223> OTHER INFORMATION: Synthetic (reverse primer of adhE2)

<400> SEQUENCE: 14
ttcccttgcg gccgcttaaa acgacttgat gtagat                                  36

<210> SEQ ID NO 15
<211> LENGTH: 468
<212> TYPE: PRT
<213> ORGANISM: Artificial Sequence
<220> FEATURE:
<223> OTHER INFORMATION: Synthetic (butyraldehyde dehydrogenase)

<400> SEQUENCE: 15

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

```
Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
        370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 16
<211> LENGTH: 454
<212> TYPE: PRT
<213> ORGANISM: Artificial Sequence
<220> FEATURE:
<223> OTHER INFORMATION: Synthetic (3K9D)

<400> SEQUENCE: 16

Leu Glu Asp Lys Asp Leu Arg Ser Ile Gln Glu Val Arg Asn Leu Ile
1               5                   10                  15

Glu Ser Ala Asn Lys Ala Gln Lys Glu Leu Ala Ala Met Ser Gln Gln
            20                  25                  30

Gln Ile Asp Thr Ile Val Lys Ala Ile Ala Asp Ala Gly Tyr Gly Ala
        35                  40                  45

Arg Glu Lys Leu Ala Lys Met Ala His Glu Glu Thr Gly Phe Gly Ile
    50                  55                  60
```

```
Trp Gln Asp Lys Val Ile Lys Asn Val Phe Ala Ser Lys His Val Tyr
 65                  70                  75                  80

Asn Tyr Ile Lys Asp Met Lys Thr Ile Gly Met Leu Lys Glu Asp Asn
                 85                  90                  95

Glu Lys Lys Val Met Glu Val Ala Val Pro Leu Gly Val Ala Gly
            100                 105                 110

Leu Ile Pro Ser Thr Asn Pro Thr Ser Thr Val Ile Tyr Lys Thr Leu
            115                 120                 125

Ile Ser Ile Lys Ala Gly Asn Ser Ile Val Phe Ser Pro His Pro Asn
            130                 135                 140

Ala Leu Lys Ala Ile Leu Glu Thr Val Arg Ile Ile Ser Glu Ala Ala
145                 150                 155                 160

Glu Lys Ala Gly Cys Pro Lys Gly Ala Ile Ser Cys Met Thr Val Pro
                165                 170                 175

Thr Ile Gln Gly Thr Asp Gln Leu Met Lys His Lys Asp Thr Ala Val
                180                 185                 190

Ile Leu Ala Thr Gly Gly Ser Ala Met Val Lys Ala Ala Tyr Ser Ser
            195                 200                 205

Gly Thr Pro Ala Ile Gly Val Gly Pro Gly Asn Gly Pro Ala Phe Ile
            210                 215                 220

Glu Arg Ser Ala Asn Ile Pro Arg Ala Val Lys His Ile Leu Asp Ser
225                 230                 235                 240

Lys Thr Phe Asp Asn Gly Thr Ile Cys Ala Ser Glu Gln Ser Val Val
                245                 250                 255

Val Glu Arg Val Asn Lys Glu Ala Val Ile Ala Glu Phe Arg Lys Gln
                260                 265                 270

Gly Ala His Phe Leu Ser Asp Ala Glu Ala Val Gln Leu Gly Lys Phe
            275                 280                 285

Ile Leu Arg Pro Asn Gly Ser Met Asn Pro Ala Ile Val Gly Lys Ser
            290                 295                 300

Val Gln His Ile Ala Asn Leu Ala Gly Leu Thr Val Pro Ala Asp Ala
305                 310                 315                 320

Arg Val Leu Ile Ala Glu Glu Thr Lys Val Gly Ala Lys Ile Pro Tyr
                325                 330                 335

Ser Arg Glu Lys Leu Ala Pro Ile Leu Ala Phe Tyr Thr Ala Glu Thr
                340                 345                 350

Trp Gln Glu Ala Cys Glu Leu Ser Met Asp Ile Leu Tyr His Glu Gly
            355                 360                 365

Ala Gly His Thr Leu Ile Ile His Ser Glu Asp Lys Glu Ile Ile Arg
            370                 375                 380

Glu Phe Ala Leu Lys Lys Pro Val Ser Arg Leu Leu Val Asn Thr Pro
385                 390                 395                 400

Gly Ala Leu Gly Gly Ile Gly Ala Thr Thr Asn Leu Val Pro Ala Leu
                405                 410                 415

Thr Leu Gly Cys Gly Ala Val Gly Gly Ser Ser Ser Ser Asp Asn Ile
            420                 425                 430

Gly Pro Glu Asn Leu Phe Asn Ile Arg Arg Ile Ala Thr Gly Val Leu
            435                 440                 445

Glu Leu Glu Asp Ile Arg
    450

<210> SEQ ID NO 17
<211> LENGTH: 411
<212> TYPE: PRT
```

```
<213> ORGANISM: Artificial Sequence
<220> FEATURE:
<223> OTHER INFORMATION: Synthetic (3MY7)
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (334)..(334)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid

<400> SEQUENCE: 17

Pro Val Thr Asn Xaa Ala Glu Leu Asp Ala Xaa Ile Ala Arg Val Lys
1               5                   10                  15

Lys Ala Gln Glu Glu Phe Ala Thr Tyr Ser Gln Glu Val Asp Lys
            20                  25                  30

Ile Phe Arg Ala Ala Ser Leu Ala Ala Asn Gln Ala Arg Ile Pro Leu
                35                  40                  45

Ala Gln Gln Ala Val Glu Ser Gly Xaa Gly Ile Val Glu Asp Lys
    50                  55                  60

Val Ile Lys Asn His Phe Ala Ser Glu Phe Ile Tyr Asn Lys Tyr Lys
65                  70                  75                  80

Asp Glu Gln Thr Cys Gly Ile Leu Thr Xaa Thr Ile Ala Glu Pro Val
                85                  90                  95

Gly Ile Ile Cys Gly Ile Val Pro Thr Thr Asn Pro Thr Ser Thr Ala
                100                 105                 110

Ile Phe Lys Ser Leu Ile Ser Leu Lys Thr Arg Asn Gly Ile Ile Phe
                115                 120                 125

Ser Pro His Pro Arg Ala Lys Asn Ser Thr Asn Asp Ala Ala Lys Leu
    130                 135                 140

Val Leu Asp Ala Ala Val Ala Ala Gly Ala Pro Lys Asp Ile Ile Gly
145                 150                 155                 160
```

Trp Ile Asp Gln Pro Ser Val Glu Leu Ser Asn Ala Leu Xaa Lys His
             165                 170                 175

Asp Asp Ile Ala Leu Ile Leu Ala Thr Gly Gly Pro Gly Xaa Val Lys
             180                 185                 190

Ala Ala Tyr Ser Ser Gly Lys Pro Ala Ile Gly Val Gly Asn Val Pro
             195                 200                 205

Val Val Ile Asp Glu Thr Ala Asp Ile Lys Arg Ala Val Ala Ser Val
             210                 215                 220

Leu Xaa Ser Lys Thr Phe Asp Asn Gly Val Val Cys Ala Ser Glu Gln
225                 230                 235                 240

Ala Val Ile Val Val Asp Glu Val Tyr Asp Glu Val Lys Glu Arg Phe
             245                 250                 255

Ala Ser His Lys Ala His Val Leu Ser Lys Thr Asp Ala Asp Lys Val
             260                 265                 270

Arg Lys Val Leu Leu Ile Asp Gly Ala Leu Asn Ala Lys Ile Val Gly
             275                 280                 285

Gln Pro Ala Thr Ala Ile Ala Glu Xaa Ala Gly Val Lys Val Pro Ala
             290                 295                 300

Asp Thr Lys Val Leu Ile Gly Glu Gly Leu Gly Lys Val Ser Tyr Asp
305                 310                 315                 320

Asp Ala Phe Ala His Glu Lys Leu Ser Pro Thr Leu Gly Xaa Phe Arg
             325                 330                 335

Ala Asp Asn Phe Glu Asp Ala Val Ala Gln Ala Val Thr Xaa Val Glu
             340                 345                 350

Ile Gly Gly Ile Gly His Thr Ser Gly Leu Tyr Thr Asn Gln Asp Val
             355                 360                 365

Asn Ala Asp Arg Ile Arg Tyr Phe Gly Asp Lys Xaa Lys Thr Ala Arg
             370                 375                 380

Ile Leu Ile Asn Ile Pro Thr Thr Ser Glu Asn Val Gly Pro Lys His
385                 390                 395                 400

Leu Ile Asn Lys Lys Thr Val Ala Lys Arg Ala
             405                 410

<210> SEQ ID NO 18
<211> LENGTH: 1149
<212> TYPE: DNA
<213> ORGANISM: Artificial Sequence
<220> FEATURE:
<223> OTHER INFORMATION: Synthetic (butanol dehydrogenase derived from
      Clostridium saccharoperbutylacetonicum)

<400> SEQUENCE: 18
atggagaatt ttagatttaa tgcatataca gagatgcttt ttggaaaggg acaaatagag      60
aagcttccag aggttttaaa aagatatggt aaaaatatat tacttgcata tggtggtgga     120
agtataaaaa agaatggact ctatgatact atccaaaagc tattgaaaga ttttaatatt     180
gttgaattaa gtggtattga accaaatcca agaattgaaa ctgtaagacg tggagttgaa     240
ctttgcagaa aaaataaagt agatgttatt ttagctgttg gtggagggag tacaatagac     300
tgctcaaagg ttatagggggc aggttattat tatgctggag atgcatggga ccttgtaaaa     360
aatccagcta aataggtga ggttttacca atagtgacag ttttaacaat ggcagctact     420
ggttctgaaa tgaatagaaa tgctgttatt tcaaagatgg atacaaatga aaagcttgga     480
acaggatcac ctaagatgat ccctcaaact tctattttag atccagaata tttgtataca     540
ttgccagcaa ttcaaacagc tgcaggttgt gctgatatta tgtcacacat atttgaacaa     600

```
tatttttaata aaactacaga tgcttttgta caagataaat ttgcggaagg tttgttgcaa    660
acttgtataa aatattgccc tgttgcttta aaggaaccaa agaattatga agctagagca    720
aatataatgt gggctagttc aatggctctt aacggacttt taggaagtgg gaaagctgga    780
gcttggactt gtcatccaat agaacatgaa ttaagtgcat tttatgatat aactcatgga    840
gtaggtcttg caattttaac tccaagttgg atgagatata tcttaagtga tgtaacagtt    900
gataagtttg ttaacgtatg gcatttagaa caaaaagaag ataaatttgc tcttgcaaat    960
gaagcaatag atgcaacaga aaaattcttt aaagcttgtg gtattccaat gactttaact   1020
gaacttggaa tagataaagc aaactttgaa agatggcaa aagctgcagt agaacatggt   1080
gctttagaat atgcatatgt ttcattaaat gccgaggatg tatataaaat tttagaaatg   1140
tcccttaa                                                            1149

<210> SEQ ID NO 19
<211> LENGTH: 382
<212> TYPE: PRT
<213> ORGANISM: Artificial Sequence
<220> FEATURE:
<223> OTHER INFORMATION: Synthetic (butanol dehydrogenase derived from
      Clostridium saccharoperbutylacetonicum)

<400> SEQUENCE: 19

Met Glu Asn Phe Arg Phe Asn Ala Tyr Thr Glu Met Leu Phe Gly Lys
1               5                   10                  15

Gly Gln Ile Glu Lys Leu Pro Glu Val Leu Lys Arg Tyr Gly Lys Asn
                20                  25                  30

Ile Leu Leu Ala Tyr Gly Gly Gly Ser Ile Lys Lys Asn Gly Leu Tyr
            35                  40                  45

Asp Thr Ile Gln Lys Leu Leu Lys Asp Phe Asn Ile Val Glu Leu Ser
        50                  55                  60

Gly Ile Glu Pro Asn Pro Arg Ile Glu Thr Val Arg Arg Gly Val Glu
65                  70                  75                  80

Leu Cys Arg Lys Asn Lys Val Asp Val Ile Leu Ala Val Gly Gly Gly
                85                  90                  95

Ser Thr Ile Asp Cys Ser Lys Val Ile Gly Ala Gly Tyr Tyr Tyr Ala
            100                 105                 110

Gly Asp Ala Trp Asp Leu Val Lys Asn Pro Ala Lys Ile Gly Glu Val
        115                 120                 125

Leu Pro Ile Val Thr Val Leu Thr Met Ala Ala Thr Gly Ser Glu Met
130                 135                 140

Asn Arg Asn Ala Val Ile Ser Lys Met Asp Thr Asn Glu Lys Leu Gly
145                 150                 155                 160

Thr Gly Ser Pro Lys Met Ile Pro Gln Thr Ser Ile Leu Asp Pro Glu
                165                 170                 175

Tyr Leu Tyr Thr Leu Pro Ala Ile Gln Thr Ala Ala Gly Cys Ala Asp
            180                 185                 190

Ile Met Ser His Ile Phe Glu Gln Tyr Phe Asn Lys Thr Thr Asp Ala
        195                 200                 205

Phe Val Gln Asp Lys Phe Ala Glu Gly Leu Leu Gln Thr Cys Ile Lys
    210                 215                 220

Tyr Cys Pro Val Ala Leu Lys Glu Pro Lys Asn Tyr Glu Ala Arg Ala
225                 230                 235                 240

Asn Ile Met Trp Ala Ser Ser Met Ala Leu Asn Gly Leu Leu Gly Ser
                245                 250                 255
```

```
Gly Lys Ala Gly Ala Trp Thr Cys His Pro Ile Glu His Glu Leu Ser
            260                 265                 270

Ala Phe Tyr Asp Ile Thr His Gly Val Gly Leu Ala Ile Leu Thr Pro
            275                 280                 285

Ser Trp Met Arg Tyr Ile Leu Ser Asp Val Thr Val Asp Lys Phe Val
    290                 295                 300

Asn Val Trp His Leu Glu Gln Lys Glu Asp Lys Phe Ala Leu Ala Asn
305                 310                 315                 320

Glu Ala Ile Asp Ala Thr Glu Lys Phe Phe Lys Ala Cys Gly Ile Pro
                325                 330                 335

Met Thr Leu Thr Glu Leu Gly Ile Asp Lys Ala Asn Phe Glu Lys Met
                340                 345                 350

Ala Lys Ala Ala Val Glu His Gly Ala Leu Glu Tyr Ala Tyr Val Ser
        355                 360                 365

Leu Asn Ala Glu Asp Val Tyr Lys Ile Leu Glu Met Ser Leu
    370                 375                 380
```